US00PP09052P

United States Patent [19]

Heursel

[11] Patent Number: Plant 9,052

[45] Date of Patent: Feb. 7, 1995

[54] HYBRID TEA ROSE PLANT NAMED MELBICO

[75] Inventor: J. Heursel, Melle, Belgium

[73] Assignee: DeRuiter's Nieuwe Rozen B.V., Hazerswoude, Netherlands

[21] Appl. No.: 147,854

[22] Filed: Nov. 4, 1993

[51] Int. Cl.[6] ..... A01H 5/00

[52] U.S. Cl. ..... Plt./12

[58] Field of Search ..... Plt. 11, 12

*Primary Examiner*—Howard J. Locker

*Attorney, Agent, or Firm*—Christie, Parker & Hale

[57] ABSTRACT

A new variety of hybrid tea rose plant having red and yellow bicolor flowers and suitable for growing under glass.

2 Drawing Sheets

SUMMARY OF THE INVENTION

The present invention relates to a new and distinct variety of rose plant of the hybrid tea rose class named 'Melbico'. The seed parent of 'Melbico' is the variety known as 'Korenlo' (U.S. Plant Pat. No. 5,679), and the pollen parent is the variety known as 'Korlingo' (U.S. Plant Pat. No. 5,846). The varietal denomination of the new variety is 'Melbico'. 'Korenlo' (commercial name 'Lorena'), 1984, is the result of 'Angelique'×seedling. Flowers are medium salmon-pink, double (about 35 petals), HT form, and larger than the new variety and with no fragrance. The foliage is medium size, medium green color, semi-glossy; and, the plant has upright growth. 'Korlingo' (commercial name Kardinal), 1986, is the result of seedling×'Flamingo'. The flowers are medium red, double (about 35 petals), and with slight fragrance. The foliage is medium size, dark, semi-glossy; and upright growth.

Among the novel characteristics possessed by this new variety which distinguish it from its parents and all other varieties of which I am aware are its attractive red and yellow bicolor flowers borne on a floriferous plant with long stems and suited for production of cut flowers under glass. The new variety can be reproduced through propagation by cuttings, grafting, budding and micropropagation.

Asexual reproduction by budding of the new variety as performed in Melle, Belgium shows that the foregoing and other distinguishing characteristics come true to form and are established and transmitted through succeeding propagations.

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Colors may vary depending upon growing conditions under different climate, soil, and cultivation conditions, and phenotypic expression may also vary with light and environmental conditions.

One of the accompanying illustrations shows cut flower form of the new variety and the other illustration shows details of the new rose variety.

DETAILED DESCRIPTION OF THE NEW VARIETY

The following is a detailed description of my new variety, with color terminology in accordance with the Royal Horticultural Society Colour Chart (RHSCC) and horticultural terminology in accordance with standard terminology used in UPOV-approved horticultural guidelines. The terminology used in color descriptions herein refers to plate numbers in the aforementioned color chart.

Parentage:

*Seed parent.*—'Korenlo' (U.S. Plant Pat. No. 5,679). Pollen parent — 'Korlingo' (U.S. Plant Pat. No. 5,846).

Class: Hybrid tea.

As can be seen in the accompanying detail illustration there is shown the top of a young shoot, 1; compound three, five and seven leaflet leaves, 2, 3, and 4 respectively; a stem 5; buds, 6 and 7; a flower 8, about one-third open; and a flower 9, more fully open. Also shown are flower stems 10, 11 and 12, with reproductive organs displayed. The other illustration shows cut flower form.

The following further horticultural observations were made of specimens grown under glass in Melle, Belgium.

FLOWER

Blooming habit: Nearly continuous.

A. Bud:

(1) *Size.*—Medium.

(2) *Form.*—Ovate (before separation of sepals); urn-shaped after sepals part.

(3) *Color.*—As sepals divide, bud color is near 15A-B to 12A with near 44A at edge and washing; deeper red coloration at bud tip and edge.

(4) *Sepals.*—Longer than green bud, generally simple to slightly foliated top — near 144A, reverse — near 147C.

(5) *Peduncle.*—Length — medium, about 0.1 to 0.2 m. Aspect — straight. Strength — erect, very strong. Color — medium green, near 147B.

B. Bloom:

*Flower.*—Medium to large size; viewed from above — irregularly rounded; viewed from side — (a) upper part of fully opened flower, flattened convex; (b) lower part of fully opened flower, flattened convex.

(1) *Size.*—Average size when fully expanded — about 12 to 13 cm.

(2) *Borne.*—Singly, one to a stem.

(3) *Form.*—High centered, exhibition type, spiral imbricated, outer petals reflex and quill to points in mid to open blooms; mid petals reflex and roll under slightly.

(4) *Petalage.*—Medium petaled under normal conditions — fully double, about 35 to 40.

(5) *Color.*—When sepals part and petals begin to unfurl, color is from near 15A and B to 12A with near 44A at margin and washing into yellow coloring in petal underside; petals' top surface tends to near 44A to 42A, with some petals more uniform in color than others and some petals showing yellow washing into red base color. Coloring toward and at point of petal attachment is yellow, near 15A to 12A. Overall tonality from a distance is very attractive red with yellow and red/yellow bicolor tones.

(6) *Pedicel.*—Average quantity of hairs or prickles.

(7) *Fragrance.*—Slight to none.

(8) *Flowers stem length.*—Nominal flower stem length is about 0.7 m.

C. Petals:

(1) *Texture.*—Crisp.

(2) *Appearance.*—Inside velvety and outside satiny.

(3) *Form and size.*—First well developed outer petals — very broad, obovate.

(4) *Arrangement.*—Regularly arranged, imbricated.

(5) *Petaloids in center.*—Few to none.

(6) *Lasting quality.*—Long lasting quality on plant, after cutting about 10 to 12 days.

REPRODUCTIVE ORGANS

A. Stamens, filaments and anthers:

*Arrangement and color.*—Regularly arranged around styles; color filaments near 19A.

B. Pollen:

*Color.*—Deep yellow, near 19A.

C. Styles: Long, stigma above mouth of receptacle, red, slight to medium hairy.

D. Stigmas: Positioned below anthers.

PLANT

A. Form: Upright to bushy.

B. Growth: Vigorous, about 1.8 m.

C. Foliage: Compound 3, 5 and 7 leaflets.

(1) *Size.*—Medium.

(2) *Quantity.*—Abundant.

(3) *Color.*—Foliage at time of first flowering — medium to dark green; juvenile foliage — red/purple, near 187A; mature leaf color — near 147A, undersurface near 147C.

(4) *Shape.*—Oval, pointed.

(5) *Texture.*—Upper side is medium glossy; underside is matte.

(6) *Edge.*—Serrate.

(7) *Serration.*—Ordinary, pointed apices.

(8) *Leaf stem.*—Color — medium green.

(9) *Stipules.*—Long, narrow, simple, medium to dark green, distinct auricle.

(10) *Leaflets.*—Cross section — slight convex; little to weak undulation at margin; terminal leaflet — blade medium length and width, rounded base; petiole — medium.

D. Wood:

(1) *New wood.*—Color — young shoots have medium anthocyanin, near 183A; coloration — reddish to purple.

(2) *Old wood.*—Color — medium green, near 147B, leaf stem near 146B.

E. Prickles (thorns):

(1) *Prickles.*—Present; quantity (main stalk) — relatively few; on laterals from stalk — relatively few; shape of upper side — concave; shape of lower side — concave. Length — significant. Color — tan to reddish tan, near 178B. Position — irregular. Number≦5 mm — few. Number–5 mm — few.

F. Disease resistance: Average resistance to mildew, black spot and rust.

I claim:

1. A new and distinct variety of rose plant of the hybrid tea rose class, substantially as shown and described.

* * * * *

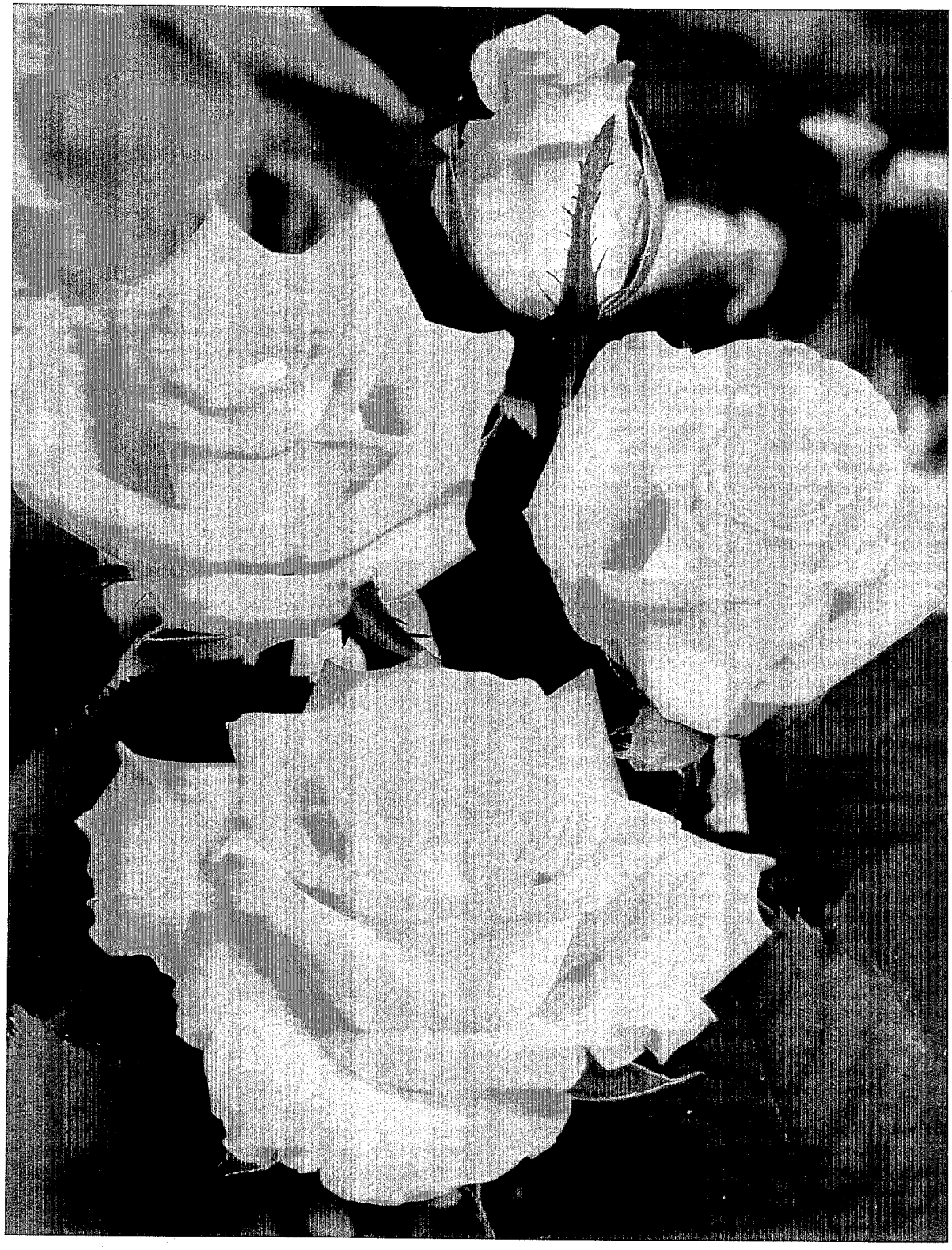

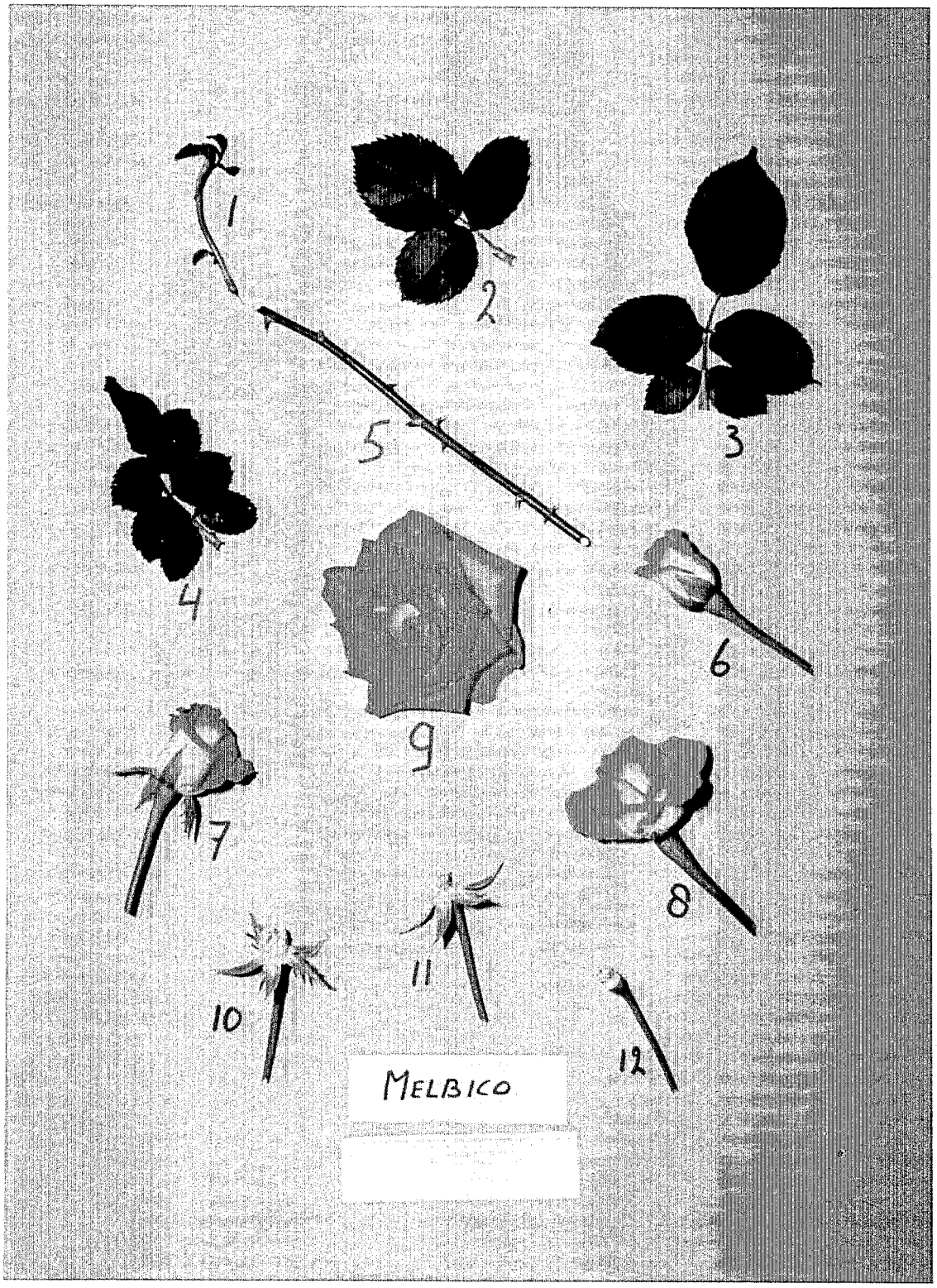
1
2
3
4
5
6
7
8
9
10
11
12
MELBICO

UNITED STATES PATENT AND TRADEMARK OFFICE

CERTIFICATE OF CORRECTION

PATENT NO. : Plant 9,052

DATED : February 7, 1995

INVENTOR(S) : J. Heursel

It is certified that error appears in the above-indentified patent and that said Letters Patent is hereby corrected as shown below:

On the title page, Item 56, References Cited, U.S. PATENT DOCUMENTS, after "[58]" insert the following references:

-- [56] References Cited

U.S. PATENT DOCUMENTS

| | | | |
|---|---|---|---|
| PP0349 | 12/1939 | Arcardi..... | Plt/12 |
| PP1012 | 5/1951 | Robinson..... | Plt/12 |
| PP6863 | 6/1989 | Perry..... | Plt/12 --. |

Signed and Sealed this

Thirty-first Day of October 1995

*Attest:*

Bruce Lehman

BRUCE LEHMAN

*Attesting Officer*

*Commissioner of Patents and Trademarks*

UNITED STATES PATENT AND TRADEMARK OFFICE

CERTIFICATE OF CORRECTION

PATENT NO. : Plant 9,052

DATED : February 7, 1995

INVENTOR(S) : J. Heursel

It is certified that error appears in the above-indentified patent and that said Letters Patent is hereby corrected as shown below:

Column 4, line 36, change "Number-5" to -- Number≥5 --.

Signed and Sealed this

Twelfth Day of March, 1996

Bruce Lehman

*Attest:*

BRUCE LEHMAN

*Attesting Officer*

*Commissioner of Patents and Trademarks*